United States Patent [19]

Asinger et al.

[11] 4,060,548

[45] * Nov. 29, 1977

[54] PROCESS OF MAKING PENICILLAMINE

[75] Inventors: Friedrich Asinger, Aachen; Heribert Offermanns, Grossauheim; Miklos Ghyczy, Laurensberg, all of Germany

[73] Assignee: Deutsche Gold- und Silber-Scheideanstalt Vormals Roessler, Frankfurt, Germany

[*] Notice: The portion of the term of this patent subsequent to Apr. 6, 1993, has been disclaimed.

[21] Appl. No.: 642,572

[22] Filed: Dec. 19, 1975

Related U.S. Application Data

[60] Division of Ser. No. 346,825, March 29, 1973, Pat. No. 3,948,984, and a continuation-in-part of Ser. No. 862,148, Sept. 4, 1969, abandoned.

[30] Foreign Application Priority Data

Sept. 6, 1968 Germany ............................ 1795297

[51] Int. Cl.² ............................................. C07C 99/10

[52] U.S. Cl. ........................ 260/534 S; 260/306.7 C; 260/306.7 R

[58] Field of Search ................................... 260/534 S

[56] References Cited

U.S. PATENT DOCUMENTS 3,948,984  4/1976  Osinger et al. .................... 260/534 S Primary Examiner—Bernard Helfin
Assistant Examiner—G. T. Breitenstein
Attorney, Agent, or Firm—Cushman, Darby & Cushman

[57] ABSTRACT

Penicillamine and its hydrochloride are made by reacting i-butyraldehyde with elemental sulfur or a sulfur-containing compound and with gaseous ammonia so as to form 2-isopropyl-5.5-dimethyl-thiazoline-$\Delta^3$, then reacting the latter compound with substantially anhydrous hydrogen cyanide so as to form the corresponding thiazolidine 4-carbonitrile, thereupon treating the latter compound with an excess of concentrated hydrochloric acid at an elevated temperature and separating the components of the mixture formed and recovering the penicillamine hydrochloride which may then be converted to the free D,L-penicillamine.

10 Claims, No Drawings

PROCESS OF MAKING PENICILLAMINE

CROSS-REFERENCES TO RELATED APPLICATIONS

This is a division of application Ser. No. 346,825 filed Mar. 29, 1973, now U.S. Pat. No. 3,948,984 which is a continuation of application Ser. No. 862,148, filed Sept. 4, 1969, now abandoned. The preparation of the thiazolines that are the starting compounds for the preparation of the penicillamine in accordance with the processes described herein is also described and claimed in application Ser. No. 855,417, filed Sept. 4, 1969, which issued as U.S. Pat. No. 3,700,683. Simultaneously with the present application the applicants are filing an application for making thiazolines--$\Delta^3$.

BACKGROUND OF THE INVENTION

The present invention relates to a process for making penicillamine and its hydrochloride. D,L-penicillamine hydrochloride has been made by hydrolysis of the corresponding thiazolidine-4-carboxylic acid ester with a semiconcentrated hydrochloric acid and a yield of about 90%. Through purification the crude penicillamine is converted with acetone to the tetramethyl-thiazolidine-4-carboxylic acid which subsequently is again split to form the pure D,L-penicillamine hydrochloride.

The thiazolidine-4-carboxylic acid ester could however be obtained only in small yields directly from the corresponding thiazolidine-4-carbonitrile or by way of the 2.2.5.5-tetramethyl-thiazolidine-4-carbonamide-hydrochloride. The tetramethyl-thiazolidine-4-carboxylic acid heretofore could not be formed directly by saponification of the corresponding thiazolidine-4-carbonitrile.

It has also been proposed to form thiazolidine-4--carbonitriles from thiazolines-$\Delta^3$ by addition of HCN. The thiazolidines-$\Delta^3$ in this case were obtained by reacting ketones with sulfur and ammonia. In a reference relating to the reaction with aldehydes yields are obtained only of 10% of thiazolines-$\Delta^3$, see the Annual Report for 1967 of Landesamt fuer Forschung des Landes Nordrhein-Westfalen, pp. 11–35.

It has accordingly not been possible to obtain penicillamine in an industrially acceptable manner in high yields starting from easily accessible starting products.

It is an object of the present invention to provide for a process of making penicillamine which solves this problem.

SUMMARY OF THE INVENTION

The process of the invention comprises the following steps:

a. reacting i-butyraldehyde with elemental sulfur or a sulfur-containing compound and gaseous ammonia or $NH_4NO_3.2NH_3$ so as to form 2-isopropyl-5.5-dimethyl-thiazoline-$\Delta^3$;

b. reacting the latter compound with substantially anhydrous hydrogen cyanide so as to form 2-isopropyl-5.5-dimethylthiazolidine-4-carbonitrile;

c. treating the latter compound with an excess of concentrated hydrochloric acid at an elevated temperature followed by d. separating the components of the resulting mixture of 2-isopropyl-5.5-dimethyl-thiazolidine-4-carboxylic acid hydrochloride, ammonium chloride and D,L-penicillamine hydrochloride and recovering the penicillamine hydrochloride therefrom.

The free D,L-penicillamine may be obtained in conventional manner from the hydrochloride.

DESCRIPTION OF THE PREFERRED EMBODIMENTS

The present invention permits to obtain pure penicillamine hydrochloride from i-butyraldehyde, sulfur or a sulfur-containing compound, ammonia or $NH_4NO_3.2NH_3$ and hydrocyanic acid with yields of 50% or more relative to the isobutyraldehyde employed as one of the starting products.

The penicillamine is useful as additive to feeds, for instance for chicks, and as a drug, for instance in the treatment of Wilson's Disease or cystinuria.

For the first stage of the process it is preferred to employ a mixture of preferably stoichiometric amounts of i-butyraldehyde, elementary sulfur and ammonia or their compounds in the presence of a flushing agent for the reaction water and in the presence of an amine. Preferably the reaction is continued for a time between about 2 and 3 hours while the reaction water is gradually removed. The reaction temperature preferably is between 50° and about 100° C.

After completion of the reaction the flushing agent, the ammonia and, if such has been used, the amine are preferably removed at a reduced pressure and recovered for further use. The 2-isopropyl-5.5-dimethyl-thiazoline-$\Delta^3$ can be purified by rectification upon exclusion of air. If a solid amine is used, it must be washed out from the reaction product, for instance by dilute acid.

The flushing agents for the reaction water may for instance be benzene, toluene, xylene, cyclohexane, a chlorinated hydrocarbon such as chloroform or methylene chloride. It is also possible to employ the aldehyde itself as the flushing agent.

The secondary or tertiary amines which may be used are preferably those which have a boiling point between about 40° and 150° C. Examples are trialkylamines such as triethylamine, pyridine, piperidine, pyrrolydine and its N-substitution derivatives such as N-methylpyrrolidine, diazadicyclooctane. The most preferred amine is pyridine.

The amines are preferably used in an amount between about 0.1 and 0.5 mol per mol of i-butyraldehyde. The amount is not critical.

The sulfur is preferably used in the form of elementary sulfur. However, it is also possible to use sulfur-containing compounds such as polysulfides or compounds of the type of the 7-phenyl-7-alkyl-amino-8-thioxo-1,2,3,4,5,6-hexathiocanes.

The reaction in this stage of the process takes place in quantitative amounts. No by-products are formed. The yield is about 80% but can be further improved by providing that no aldehyde escapes with the ammonia from the reaction vessel. This can be accomplished, for instance, by washing out or freezing of the aldehyde found in the exhaust gas and recirculation thereof or otherwise by employing a slight pressure.

The reaction water during this stage of the procedure is removed by azeotropic distillation.

In the second stage of the process, it is possible to employ an excess of substantially anhydrous hydrocyanic acid. It is however preferred to use the acid only in a stoichiometric amount or about such an amount. The nitrile is then obtained in quantitative yields.

In this stage of the process, it is possible for instance to proceed as follows: The thiazoline-$\Delta^3$ is reacted with dry ether, preferably a petrolether, and anhydrous hydrogen cyanide is then blown into the mass while cooling the temperature to below about 10° C. The acid should preferably be free of stabilizers.

The reaction should in general last about 2 to 4 hours at room temperature. Thereafter the temperature is cooled to below about −30° C and the nitrile is removed by suction.

The crude nitrile product can either be used as such for the next stage of the process or may be subjected to an intermediate purification, for instance by precipitation from petrolether.

If there is an excess of hydrogen cyanide after the completion of this stage, it may be removed and the compound may then be converted to the hydrochloride.

There is thus obtained in this second stage of the process either a crude nitrile, or a purified nitrile or a hydrochloride thereof. This product is then heated for a few hours, if desired under pressure, with an excess of concentrated hydrochloric acid and upon exclusion of oxygen. The temperature to be reached is between about 70° and 110° C. Preferably an amount of about 300 to 500 ml of concentrated hydrochloric acid is used per mol of nitrile compound. If this reaction is started from the free nitrile compound, it is preferable to replenish the reaction mass with gaseous hydrogen chloride corresponding to the amount of hydrochloride formation occurring. After completion of the reaction, the mixture is concentrated by evaporation at a reduced pressure.

There is thus obtained a mixture which for brevity will be designated herein as A and which consists of 2-i-propyl-5.5-dimethyl-thiazolidine-4-carboxylic acid hydrochloride, ammonium chloride and small amounts of D,L-penicillamine hydrochloride.

From this mixture the penicillamine hydrochloride may be obtained by separation of the components and recovery of the desired product in various manners.

Preferably the mixture is first brought to boiling point in a liquid water-miscible carbonyl compound which preferably is acetone. The carbonyl compound will be designated herein as B. After cooling the mass, it is subjected to suction and the obtained solid material may then be further treated for extraction purposes, with a carbonyl compound as designated B, followed by subjecting of the extract to a steam distillation.

Preferably, the solid material is immediately steam-distilled, followed by concentration by evaporation to dryness of the residue, whereupon the ammonium chloride is separated out by extraction with an alcohol. Another preferred way of extraction following the steam distillation and concentration by evaporation by evaporation to dryness is by means of treating and extraction the residue with the carbonyl compound B and finally boiling extract with water. The alcohol preferably is anhydrous methanol, ethanol or isopropanol. It is also possible to subject the mixture A directly to treatment with anhydrous methanol, ethanol or isopropanol followed by a steam distillation. Likewise, the mixture A without previous evaporation can directly be subjected to the steam distillation followed by an extraction with an alcohol or carbonyl compound as described above.

There is thus obtained D,L-penicillamine hydrochloride which may be converted in conventional manner to the free D,L-penicillamine.

The steam distillation used in the separation and extraction step is preferably carried out in the presence of small amounts of hydrochloric acid. The extraction preferably is performed in a soxhlet apparatus.

The conversion of the salt to the free acid can be effected by treatment with an alkali hydroxide or a hydrogen carbonate or by means of ion-exchange compounds.

Finally, the racemic mixture obtained may be separated, for instance, by reaction with Brucin.

The following examples will further illustrate the invention.

EXAMPLE 1 a. A mixture of 144 g (2 mol) isobutyraldehyde, 1.0 mol pyridine, 32 g (1 g-atom) of elemental sulfur and 120 ml of benzene were heated for 2½ to 3 hours while introducing ammonia (about 1.2 mol) and azeotropically removing the reaction water. Since ammonia is dissolved in the reaction water there are obtained about 40 ml.

The benzene and the amine are drawn off at a slightly reduced pressure and the obtained 2-isopropyl-5.5-dimethylthiazoline-$\Delta^3$ is subjected to rectification. The yield is about 80% of the theoretical yield. Boiling point: 60° C, $n_D^{20} = 1.4782$; picrate melting point 116° C.

b. 157 g (1 mol) of 2-isopropyl-5.5-dimethylthiazoline-$\Delta^3$ were mixed with 120 ml petrolether (30/70). The mass was then cooled to obtain a reaction temperature of 5° C and 30 g (about 1.1 mol) of substantially anhydrous hydrocyanic acid was applied by blowing into the mass during a period of about 1¼ hours. The hydrocyanic acid was free of stabilizers (distilled). The reaction was then permitted to proceed for another 2 hours at room temperature. After cooling to −30° to −40° C and application of suction by means of a precooled suction filter there were obtained 175 g (95%) of the crude 2-isopropyl-5.5-dimethyl-thiazolidine-4-carbonitrile. After purification by precipitation from petrolether the product had a melting point of 31° C. The chlorhydrate melting point is at 150°-152° C (decomposition).

c. 184.3 g (1 mol) 2-isopropyl-5.5-dimethylthiazolidine-4-carbonitrile were reacted with 500 ml concentrated hydrochloric acid (density 1.19). Hydrogen chloride is then introduced into the mixture to replenish the amount used up by the hydrochloride formation. The mass is thereafter heated for about 40 hours to 105° C. (temperature in the vapour phase) while a weak nitrogen flow is passed through the vessel). After concentration to dryness by evaporation at a reduced pressure, there is obtained a mixture from crude 2-isopropyl-5.5-dimethyl-thiazolidine-4-carboxylic acid hydrochloride and ammonium chloride containing a small amount of D,L-penicillamine hydrochloride.

d. The mixture obtained is subjected to brief boiling with about 400 ml acetone and after cooling to about 0° C, is subjected to sudden strong suction. There is thus obtained a crystalline mass which is subjected to a steam distillation after adding 4 g of activated carbon. As soon as carbonyl compound is no longer found in the distillate (about 5 liters), the activated coal is filtered off in a nitrogen atmosphere and the mass is then concentrated by evaporation to dryness at a reduced pressure. There is obtained a mixture of D,L-penicillamine hydrochloride and ammonium chloride.

The penicillamine hydrochloride is separated from the only slightly soluble ammonium chloride by means of about 200 ml abs. ethanol. After evaporation of the ethanol the penicillamine hydrochloride is dissolved in a small amount of water and heated with about 1.5 to 2 l butyl acetate while gradually removing the water by distillation. After evaporation of the butyl acetate there are obtained 128 g of pure D,L-penicillamine hydrochloride of a melting point of 139°-141° C.

Accordingly, 128 g of D,L-penicillamine hydrochloride were obtained from 157 g (1 mol) of 2-isopropyl-5.5-dimethylthiazoline-$\Delta^3$. This constitutes a yield of 70%. Relative to the isobutyraldehyde employed in the reaction, the yield is thus about 50%.

EXAMPLE 2

The steps (a) and (b) were the same in this example as in Example 1. However, in this case, slightly different amounts were used and the hydrochloride was formed. In the next step 220.8 g (1 mol) of 2-isopropyl-5.5-dimethylthiazolidine-4-nitrile hydrochloride was heated upon exclusion of air for 40 hours with 300 ml of concentrated hydrochloric acid (density: 1.19). The steam temperature was 106° C. After completion of the reaction, the reaction mixture was concentrated almost to dryness by evaporation at reduced pressure. There were then added 300 ml of acetone and the mass was heated 10 minutes upon reflux and subsequently cooled to 0° C. After vigorous abrupt suction the reaction product which was almost colorless was placed in a 1-liter 2-neck flask, was reacted with 600 ml of distilled water, 10 ml of concentrated hydrochloric acid and about 2 g of activated carbon. It was then subjected to a steam distillation. After obtaining about 5 liters of condensate liquor, the steam distillation was ended. The activated carbon was removed by filtration in a nitrogen atmosphere and the mass was concentrated by evaporation to dryness. The remaining colorless crystalline mass was a mixture of D,L-penicillamine hydrochloride and ammonium chloride.

This mass was then placed in a Soxhlet extraction thimble and subjected for several hours to extraction with acetone. After evaporating the extracting agent, there were obtained 192 g (85%) of the acetone adduct of the D,L-penicillamine hydrochloride (2.2.5.5-tetramethyl-thiazolidine-4-carboxylic acid hydrochoride) which was contaminated with at most 1.5% ammonium chloride. The acetone adduct had a melting point of 204° C. The D,L-penicillamine hydrochloride was obtained from the acetone adduct by heating for 30 minutes with distilled water.

EXAMPLE 3

This example illustrates only a slight variation in the first stage identified as a (in Example 1).

In a four-neck flask provided with a stirrer, a gas inlet with frit, thermometer and water separator, 721 g (10 mol) of isobutyraldehyde and 128 g (4 gram atom) of sulfur were placed together with ammonia until the distillation of the reaction water was complete. The temperature initially was 60° C and, towards the end of the reaction, increased to 90° C, while the temperature of the oil bath was maintained at 120° C. After cooling of the contents of the flask to room temperature, distillation was effected in a 1 m long column. The thiazoline distilled over after 10 ml as a yellow liquid which could be made colorless by distillation over sodium. Yield: 557 g = 71%. Boiling point: 67°-68° C (14 Torr).

We claim:

1. In a process for the production of D,L-penicillamine or its hydrochloride by reacting 2-isopropyl-5,5-dimethylthiazoline-3 with hydrogen cyanide to form 2-isopropyl-5,5-dimethylthiazoline-4-carbonitrile, hydrolysis of the nitrile with hydrochloric acid to form 2-isopropyl-5,5-dimethylthiazolidine-4-carboxylic acid hydrocloride and converting said 2-isopropyl-5,5-dimethylthiazolidine-4-carboxylic acid hydrochloride to penicillamine hydrochloride the improvement consisting of:
   a. reacting 2-isopropyl-5,5-dimethylthiazoline-3 with substantially anhydrous hydrogen cyanide to form said thiazolidine carbonitrile,
   b. heating said thiazolidine carbonitrile with excess concentrated hydrochloric acid at a temperature between about 70° C. and 110° C. to form said thiazolidine carboxylic acid hydrochloride, and,
   c. converting said thiazolidine carboxylic acid hydrochloride to penicillamine hydrochloride by subjecting it to a steam distillation.

2. The process of claim 1 wherein step (a) is carried out at a temperature below about 10° C.

3. The process of claim 2 wherein in step (a) said thiazoline is employed dissolved in an invert solvent.

4. The process of claim 1 wherein step (a) said thiazoline is employed dissolved in an invert solvent.

5. The process of claim 1 wherein in converting the thiazoline to the thiazolidine carbonitrile in step (a) there is employed hydrogen cyanide in an about stoichiometric amount or in an amount in excess of that stoichiometrically required to convert the said thiazoline to said thiazolidine carbonitrile.

6. The process of claim 5 wherein the hydrogen cyanide is employed in an about stoichiometric amount to the thiazoline.

7. The process of claim 1 wherein the steam distillation in step (c) is carried out in the presence of small amounts of hydrochloric acid.

8. The process of claim 1 including the step of recovering the D,L-penicillamine hydrochloride from the residue of the steam distillation.

9. The process of claim 1 wherein the product formed in step (b) containing said thiazolidine carboxylic acid hydrochloride, is subjected directly to said steam distillation step (c).

10. The process of claim 1 wherein the product formed in step (b) containing said thiazolidine carboxylic acid hydrochloride, is treated with acetone prior to step (c).

* * * * *

UNITED STATES PATENT OFFICE
CERTIFICATE OF CORRECTION

Patent No. 4,060,548          Dated Nov. 29, 1977

Inventor(s) Friedrich ASINGER, Heribert OFFERMANNS and Miklos GHYCZY

It is certified that error appears in the above-identified patent and that said Letters Patent are hereby corrected as shown below:

[60] Division of Ser. No. 346,825, March 29, 1973, Pat. No. 3,948,984, and a continuation of Ser. No. 862,148, Sept. 4, 1969, abandoned.

Signed and Sealed this

Twenty-eighth Day of March 1978

[SEAL]

Attest:

RUTH C. MASON
*Attesting Officer*

LUTRELLE F. PARKER
*Acting Commissioner of Patents and Trademarks*